United States Patent [19]

Silbering et al.

[11] Patent Number: 4,477,428

[45] Date of Patent: Oct. 16, 1984

[54] ORAL COMPOSITIONS COMPRISING $N^\alpha, N^G$-DIACYL DERIVATIVES OF ARGININE

[75] Inventors: Steven B. Silbering, Plainsboro; Tibor Sipos, Lebanon, both of N.J.

[73] Assignee: Johnson & Johnson Products, Inc., New Brunswick, N.J.

[21] Appl. No.: 412,041

[22] Filed: Aug. 26, 1982

[51] Int. Cl.³ .................. A61K 7/22; C07C 129/12
[52] U.S. Cl. ........................... 424/52; 424/54; 260/404.5; 562/560
[58] Field of Search .............. 562/560; 260/404.5; 424/52, 54

[56] References Cited

U.S. PATENT DOCUMENTS 2,772,203  11/1956  Salzmann .................... 424/54

OTHER PUBLICATIONS

Yoshida, Chem. Abst. 85:110386t, (1976).
"Beilsteins Handbuch der Organischen Chemie," 2nd Supp., vol. 4, pp. 1354 and 1361, (1963).
"Beilsteins Handbuch der Organischen Chemie," 3rd Supp., vol. 4, p. 2652, (1980).

*Primary Examiner*—Michael L. Shippen
*Attorney, Agent, or Firm*—Wayne R. Eberhardt

[57] ABSTRACT

Oral hygiene formulations incorporating $N^\alpha, N^G$-diacyl derivatives of arginine, or the pharmaceutically acceptable salts thereof, optionally in combination with fluoride compounds, are effective in combatting microorganisms, inhibiting acid production and reducing dental caries.

23 Claims, No Drawings

ORAL COMPOSITIONS COMPRISING $N^\alpha, N^G$-DIACYL DERIVATIVES OF ARGININE

FIELD OF THE INVENTION

The present invention relates to compositions of matter having utility in maintaining oral health. It also relates to methods of making such compositions, and the incorporation of same into pharmaceutically suitable vehicles for use in oral health care. More particularly, the invention relates to diacyl derivatives of arginine, optionally in combination with fluoride compounds, and their utility in maintaining oral health.

BACKGROUND OF THE INVENTION

It has been shown that tooth decay and dental disease can be attributed to bacteria forming plaque about the teeth. Growth and proliferation of bacteria is enhanced by the presence of entrapped food particles between the teeth. The removal of plaque and entrapped food particles reduces caries, reduces the tendency towards gingivitis, and reduces mouth odor as well as generally improving oral hygiene.

The prior art recognizes mechanical oral hygiene devices serving to clean the mouth of debris and remove plaque from teeth, such as toothbrushes, flosses, and toothpicks. It also recognizes compositions mostly used in conjunction with such devices but which impart a chemical action in cleaning teeth, such as dentifrices and rinses. In addition to these, various dental coatings and sealants have been applied to teeth as barriers against bacterial action and plaque formation. Another important approach in oral care includes the use of various fluoride-containing preparations which are able to deposit fluoride ions directly onto the surface of tooth enamel. While great advances were made in oral health care by the use of these various approaches, none seem to be completely effective.

A more recent approach to improved oral hygiene involves the recognition that bacteria present in the oral cavity metabolize dietary sugars, such as glucose and sucrose, to organic acids, such as acetic, propionic and lactic acids. The production of these acids results in a rapid drop in plaque pH. If the pH drops to a level of about 5.5 or below and remains there for more than a short period of time, the tooth enamel will begin to demineralize. This process, if repeated over a substantial period of time, will eventually lead to the development of caries. To correct for the pH drop, the saliva contains a pH-rise factor which moderates the extent and duration of the pH drop when glucose and sucrose are metabolized by oral bacteria. This factor was identified as an arginine-containing tetrapeptide. See, for example, Kleinberg, I., Kanapka, J. A., and Craw, D. "Effect of Saliva and Salivary Factors on the Metabolism of the Mixed Oral Flora" *Microbial Aspects of Dental Caries*, Vol. II, pp. 433–464 (1976). This pH-rise factor is believed to enter the bacterial cell and either neutralize the organic acids as they form or alter bacterial metabolism so that the acids are not produced.

DISCUSSION OF THE PRIOR ART

U.S. Pat. No. 2,689,170 to King, entitled "Oral Preparation for Inhibition of Dental Caries", discloses oral preparations for inhibition of dental caries having as the active ingredient a saturated higher series of alkyl acyl amide of a saturated aliphatic monoaminocarboxylic acid compound.

U.S. Pat. No. 4,154,813 to Kleinberg, entitled "Means and Method for Improving Natural Defenses Against Caries", discloses a method for supplementing the body's resistance to caries by providing a pH-rise factor which is a peptide of 2–4 amino acid units, one or more of which is arginine.

U.S. Pat. No. 4,225,579 to Kleinberg, entitled "Means and Method for Improving Defenses Against Caries", claims peptides of 2–4 amino acid units, one or more of which is arginine, for combatting caries. These arginine-containing peptides are disclosed to penetrate dental plaque and bacteria in the mouth and to counteract acid produced as a result of metabolism of carbohydrates.

British Pat. No. 1,352,420 to Yoshinaga et al, entitled "Novel Arginine Derivatives, Their Production and Their Use", discloses $N^\alpha$-acylarginines having antibacterial or germicidal properties for use in oral hygiene.

U.S. Pat. No. 3,809,759 to Bocher and Faure, entitled "Pharmaceutical Composition for Treating Mental Fatigue Containing Arginine-Potassium Phospho-citro-glutamate and Method of using the Same", discloses arginine-potassium phospho-citro-glutamate in pharmaceutical compositions, such as, granules, pills, tablets, and capsules for systemic treatment of mental fatigue.

U.S. Pat. No. 4,061,542 to Demny and Maehr, entitled "2-Methyl-L-Arginine produced by Cultivating Streptomyces Strain", discloses the title compound for use as an antibiotic and antibacterial agent.

U.S. Pat. No. 4,125,619 to Okamoto et al, entitled "$N^\alpha$-Naphthalenesulfonyl-L-Arginine Derivatives and the Pharmaceutically Acceptable Acid Addition Salts Thereof", discloses the title compounds for use as pharmaceutical agents for the inhibition and suppression of thrombosis.

Some long-chain $N^G$-acyl derivatives of arginine are described in the chemical literature. See for example, Guttmann, St. and Pless, J. "On the Protection of the Guanidino Group of Arginine", *Acta Chim Acad. Sci. Hung* 44 (1–2), 23–30 (1965). The acyl groups are temporarily placed on the arginine molecule at the $N^G$-position and serve as temporary blocking or protecting groups which are subsequently removed from the $N^G$-position when the appropriate substituents are placed on the $N^\alpha$-position of arginine. These blocking groups thus serve to protect the $N^G$-position from chemically reacting while the nitrogen atom at the $N^\alpha$-position participates in the chemical reaction.

The compounds of the present invention differ from the aforementioned prior art in that we use new and novel derivatives of arginine in which the polar character of the arginine molecule is modified by the presence of lipid-like substituents. This modification is believed to permit such arginine derivatives to more readily penetrate the phospholipid-containing cell wall of oral bacteria and to inhibit acid production of these bacteria.

Accordingly, one object of the present invention is to provide new and novel derivatives of arginine.

Another object of the present invention is to provide compositions containing an arginine derivative for use in oral applications.

Still another object of the present invention is to provide compositions containing an arginine derivative in combination with a fluoride compound for use in oral applications.

It is still a further object of the present invention to provide methods of preparing such compounds and compositions.

SUMMARY OF THE INVENTION

Oral compositions of the present invention comprise $N^\alpha$, $N^G$-disubstituted acyl derivatives of arginine of the formula:

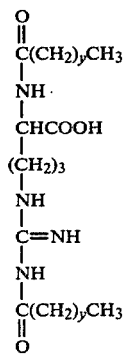

where y is an integer from 0 to about 28, preferably from about 4 to about 18, and most preferably from 8 to 14.

The $N^\alpha,N^G$-diacyl derivatives of arginine where y is not more than about 18 are preferred since these derivatives possess greater activity against oral bacteria than the higher members of the series.

In general $N^\alpha,N^G$-diacylarginines may be prepared by dissolving L-(+)-arginine in a solution of 3 parts water and 2 parts acetone, and thereafter simultaneously adding sodium hydroxide and a solution of an aliphatic acid chloride and reacting the mixture at room temperature. The mole ratio of the L-(+)-arginine to the aliphatic acid chloride must be 1:2. The reaction is allowed to proceed at room temperature for about 24 hours whereafter the product is precipitated by adjusting the pH to 6 with glacial acetic acid. The precipitate is collected and recrystallized from an organic solvent such as methanol or ethanol.

The present invention also encompasses pharmaceutically acceptable salts of the $N^\alpha,N^G$-diacyl derivatives of arginine such as those formed by reaction of an organic or inorganic base with the acidic (—COOH) portion of the diacylarginine molecule, and those formed by reaction of an organic or inorganic acid with the guanidino portion of the acylarginine molecule. Typical salts are those of the formula

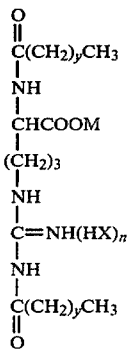

wherein y is an integer of from 0 to about 28; M is H, Na, K, Mg, Ca, Ag, Ce, Mn, Zn or the residue of a strong organic base; n is 0 or 1; and HX is HCl, HNO₃, H₂SO₄, CH₃COOH or gluconic acid

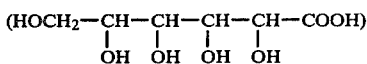

The present invention provides oral compositions of an $N^\alpha,N^G$-diacyl derivative of arginine in the form of a mouthwash, spray, dentifrice, gel, powder, solution, lotion, varnish, lozenge, chewing gum, slow releasing device and the like for use in oral hygiene in combatting bacteria and to increase pH of the oral fluids.

The present invention further provides oral compositions of $N^\alpha,N^G$-diacyl derivatives of arginine with a fluoride compound, such as, sodium fluoride, zinc fluoride, stannous fluoride, sodium monofluorophosphate, acidulated phosphate fluoride, ammonium fluoride, ammonium bifluoride and amine fluoride.

DETAILED DESCRIPTION OF THE INVENTION

The process for preparing compounds of this invention and oral compositions comprising such compounds are illustrated by the following specific examples, which are not intended to be limiting of the invention.

EXAMPLE 1

$N^\alpha,N^G$-dilauroylarginine

Two grams (0.01148 mole) of L-(+) arginine were dissolved in a solution of 30 ml of water and 20 ml of acetone. To this solution were added, at room temperature, 10 ml of a 5M sodium hydroxide solution, followed immediately by the addition of one-half of a solution prepared by dissolving 5.02 gram (0.02296 mole) of lauroyl chloride in 10 ml of acetone. Fifteen minutes later, identical portions of the sodium hydroxide and lauroyl chloride solutions were added. The reaction mixture was allowed to stir overnight. The pH of the reaction mixture was then adjusted to 6 with glacial acetic acid which resulted in the precipitation of a white solid. The solid was collected by filtration and was washed with water. The washed solid then was air-dried and recrystallized from chloroform-acetone. The yield of $N^\alpha,N^G$-dilauroylarginine having the formula below was 0.980 gram (24.4%).

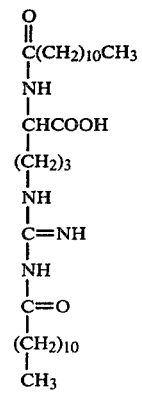

Exactly the same procedure was used to prepare the following $N^\alpha,N^G$-diacyl derivatives of arginine:

$N^\alpha,N^G$-dioctanoylarginine: (C₈)

$N^\alpha,N^G$-didecanoylarginine: ($C_{10}$)
$N^\alpha,N^G$-dimyristoylarginine: ($C_{14}$)
$N^\alpha,N^G$-dipalmitoylarginine: ($C_{16}$).

Representative compounds of the present invention were assayed to determine their effectiveness in reducing acid production from sugar by *S. mutans* as a measure of their efficacy in oral compositions.

ASSAY FOR INHIBITORS OF GLYCOLYSIS

This assay measures the rate of acid production from the metabolism of sucrose by *Streptococcus mutans* 6715. The assay solution consists of 10.00 ml of a phosphate buffer at pH 5.5 under nitrogen. To this solution are added $8 \times 10^9$ cells of *S. mutans* 6715, followed by 50 μl of $25 \times 10^{-3}$M sucrose. A known volume of a 10 mg/ml solution of the test arginine derivative is then added, and the rate of acid production is monitored with the automatic addition of a $5 \times 10^{-3}$N KOH solution by a pH-stat.

Table I illustrates acid inhibition activity of the indicated compounds in terms of the concentration of compound required to effect a 50% reduction in the rate of acid formation.

TABLE I

| Arginine Derivative | Concentration (W/V %) |
|---|---|
| $N^\alpha,N^G$—didecanoylarginine | 1.0 |
| $N^\alpha,N^G$—dilauroylarginine | 0.45 |
| $N^\alpha,N^G$—dimyristoylarginine | 1.0 |

Oral compositions of the present invention include the combination of $N^\alpha,N^G$-diacyl derivatives of arginine with a fluoride compound, e.g. sodium fluoride, zinc fluoride, stannous fluoride, sodium monofluorophosphate, acidulated phosphate fluoride, ammonium fluoride, ammonium bifluoride and amine fluoride. In general, the $N^\alpha,N^G$-diacyl derivative of arginine should be present in an effective amount up to a saturated solution, while the fluoride ion should be present from as low as 0.0001% to 10%.

The preferred concentration of $N^\alpha,N^G$-diacyl derivative of arginine is 0.05 to 10%, while that of the fluoride ion is 0.001 to 1.0%. The most preferred concentration of the arginine derivative is 0.5 to 5%, and the fluoride ion, 0.01 to 0.1%. While higher concentrations of both $N^\alpha,N^G$-diacyl derivatives of arginine and fluoride ions could be used, no particular advantage is afforded thereby.

While it is presently preferred to have a polyol-containing aqueous vehicle as an acceptable carrier for the above composition, other nonaqueous compositions are not excluded from the list of suitable carriers, as for example various alcohols, polyols, and dimethylsulfoxide.

The composition of this invention may be in the form of a mouthwash, spray, dentifrice, gel, powder, solution, lotion, varnish, lozenge, chewing gum, slow releasing device or other forms suitable for oral application. Any pharmaceutically acceptable materials such as those ordinarily used in such oral compositions that are compatible with $N^\alpha,N^G$-diacyl derivatives of arginine and fluoride ions may be employed in the compositions of this invention.

In accordance with the present invention, the compositions are supplied to teeth with an appliance, e.g., toothbrush, swab, impregnated dental floss and the like by gently brushing the teeth, both the buccal and linqual sides, at least once daily. The most preferred application of the above compositions to teeth is from lozenge and from chewing gum, whereby one slowly dissolves the lozenge in the mouth over 10 to 15 minutes, and by chewing the gum over 30 to 45 minutes after each meal.

The following examples will further serve to illustrate typical oral compositions of this invention.

EXAMPLE 2 (Mouthrinse)

| | w/w % |
|---|---|
| Glycerol, U.S.P. | 10 to 40 |
| $N^{\alpha,G}$—diacylarginine | 0.1 to 5 |
| NaF | 0.2 |
| Flavors | 1.0 |
| Preservatives | 0.3 |
| Pluronic F-108 | 2.0 |
| Water, q.s. to 100 parts | |

The $N^\alpha,N^G$-diacyl derivative of arginine was dissolved in water with continuous stirring at 80° C. The remaining ingredients were dissolved in glycerol and mixed with the $N^\alpha,N^G$-diacylarginine solution at room temperature.

EXAMPLE 3 (Gel Dentifrice)

| | w/w % |
|---|---|
| Pluronic F-127 | 20.0 |
| Flavors | 0.8 |
| Preservatives | 0.3 |
| $N^\alpha,N^G$—diacylarginine | 2.0 |
| Water, q.s. to 100 parts | |

EXAMPLE 4 (Gel Dentifrice)

| | w/w % |
|---|---|
| $N^\alpha,N^G$—diacylarginine | 2.0 |
| NaF | 0.2 |
| Pluronic F-127 | 20.0 |
| Flavors | 0.8 |
| Preservatives | 0.3 |
| Water, q.s. to 100 parts | |

The gels of Examples 3 and 4 were prepared as follows:

The $N^\alpha,N^G$-diacylarginine was dissolved in 50 ml water while continuously stirring at 80° C. After the arginine derivative had dissolved, the solution was cooled to room temperature and the NaF (if present) and preservatives were added. Separately, the Pluronic F-127 and flavors were dissolved at 4° C. The solution was allowed to warm up to room temperature and then blended into the arginine containing solution with continuous stirring. The mixture was homogenized and the pH of the gel adjusted to 5.5 by the addition of NaOH or HCl as required.

EXAMPLE 5 (Paste Dentifrice)

| | w/w % |
|---|---|
| $N^\alpha,N^G$—diacylarginine | 1 to 5 |
| NaF | 0.2 |
| Glycerol | 15.0 |
| Sorbitol | 10.0 |
| Sodium lauryl sulfate | 1.2 |
| Calcium pyrophosphate | 40.0 |

-continued

| | w/w % |
|---|---|
| Propylene glycol | 10.0 |
| Flavors | 1.0 |
| Preservatives | 0.3 |
| Pluronic F-127 | 10.0 |
| Water, q.s. to 100 parts | |

The $N^\alpha,N^G$-diacylarginine was dissolved in glycerol, sorbitol, propylene glycol, Pluronic F127 and water at 80° C. The pH was adjusted to 5.5 and the flavors, NaF, preservatives and sodium lauryl sulfate were added. The calcium pyrophosphate was blended into the mixture with continuous stirring at room temperature, and the mixture was homogenized with a roller mill. In this formulation, the sodium fluoride component is optional and may be omitted in the preparation of a nonfluoride dentifrice.

EXAMPLE 6 (Powder Dentifrice)

| | w/w % |
|---|---|
| $N^\alpha,N^G$—diacylarginine | 1 to 5 |
| Flavors | 4.0 |
| Sodium lauryl sulfate | 2.0 |
| Saccharin | 0.4 |
| Abrasive, q.s. to 100 parts | |

EXAMPLE 7 (Lozenge)

| | w/w % |
|---|---|
| $N^\alpha,N^G$—diacylarginine | 1 to 5 |
| Sorbitol | 20.0 |
| Mannitol | 20.0 |
| Starch | 12.0 |
| Flavors | 2.0 |
| Preservatives | 0.4 |
| Saccharin | 0.2 |
| Magnesium stearate | 0.8 |
| Talc | 0.5 |
| Corn syrup, q.s. to 100 parts | |

The mixture of Example 7 was granulated into a homogeneous blend and pressed into a lozenge.

Although the present invention has been described with reference to particular embodiments and examples, it will be apparent to those skilled in the art that variations and modifications of this invention can be made and that equivalents can be substituted therefore without departing from the principles and the true spirit of the invention.

We claim:

1. $N^\alpha,N^G$-diacyl derivatives of arginine having the formula:

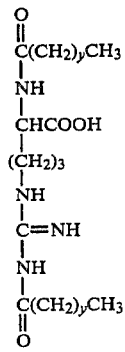

where y is an integer of from 0 to 28, and the pharmaceutically acceptable salts thereof.

2. A compound of claim 1 wherein said pharmaceutically acceptable salts are selected from the group consisting of alkali metal salts, alkaline earth metal salts, amphoteric metal salts, heavy metal salts, organic base salts, and organic and inorganic acid salts.

3. The compound of claim 1 wherein said derivative of arginine is $N^\alpha,N^G$-dioctanoylarginine.

4. The compound of claim 1 wherein said derivative of arginine is $N^\alpha,N^G$-didecanoylarginine.

5. The compound of claim 1 wherein said derivative of arginine is $N^\alpha,N^G$-dilauroylarginine.

6. The compound of claim 1 wherein said derivative of arginine is $N^\alpha,N^G$-dimyristoylarginine.

7. The compound of claim 1 wherein said derivative of arginine is $N^\alpha,N^G$-dipalmitoylarginine.

8. A composition of matter for oral hygiene to inhibit acid production by microorganisms in the oral cavity comprising an effective amount, in a pharmaceutically acceptable carrier, of an $N^\alpha,N^G$-diacyl derivative of arginine having the formula;

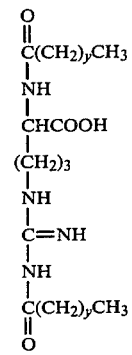

wherein y is an integer of from 0 to 28, or a pharmaceutically acceptable salt thereof.

9. The composition of matter of claim 8 wherein said derivative of arginine is $N^\alpha,N^G$-dioctanoylarginine.

10. The composition of matter of claim 8 wherein said derivative of arginine is $N^\alpha,N^G$-didecanoylarginine.

11. The composition of matter of claim 8 wherein said derivative of arginine is $N^\alpha,N^G$-dilauroylarginine.

12. The composition of matter of claim 8 wherein said derivative of arginine is $N^\alpha,N^G$-dimyristoylarginine.

13. The composition of matter of claim 8 wherein said derivative of arginine is $N^\alpha,N^G$-dipalmitoylarginine.

14. The composition of matter of claim 8 wherein said pharmaceutically acceptable carrier is a dentifrice.

15. The composition of matter of claim 8 wherein said pharmaceutically acceptable carrier is a lozenge.

16. A composition of matter for oral hygiene to inhibit the formation of caries comprising, in a pharmaceutically acceptable carrier, from about 0.0001% to about 10% of a fluoride salt and an effective amount of an $N^\alpha,N^G$-diacyl derivative of arginine having the formula:

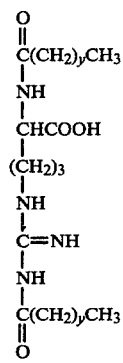

wherein y is an integer of from 0 to 28, or a pharmaceutically acceptable salt thereof.

17. The composition of matter of claim 16 wherein said pharmaceutically acceptable carrier is a mouthrinse.

18. The composition of matter of claim 16 wherein said pharmaceutically acceptable carrier is a dentifrice.

19. A composition of matter for oral hygiene to inhibit the formation of caries comprising from about 0.05 to about 10% of $N^\alpha,N^G$-diacyl derivative of arginine having the formula:

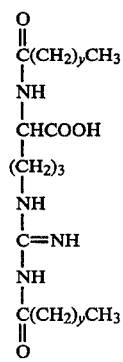

whereby y is an integer of from 4 to 18, or a pharmaceutically acceptable salt thereof, in combination with from about 0.001 to about 1.0% of a fluoride salt in a pharmaceutically acceptable polyol-containing vehicle.

20. The composition of matter of claim 19 wherein said derivative of arginine is $N^\alpha,N^G$-didecanoylarginine.

21. A method for inhibiting acid production by microorganisms in the oral cavity which comprises introducing into the oral cavity in a pharmaceutically acceptable carrier, an effective amount of an $N^\alpha,N^G$-diacyl derivative of arginine having the formula:

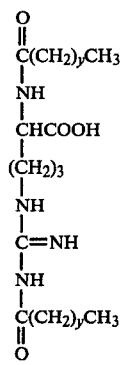

wherein y is an integer of from 0 to 28, or a pharmaceutically acceptable salt thereof.

22. A method for inhibiting acid production by microorganisms in the oral cavity which comprises introducing into the oral cavity a composition comprising, in a pharmaceutically acceptable carrier, from about 0.0001% to about 10% of a fluoride salt and an effective amount of an $N^\alpha,N^G$-diacyl derivative of arginine having the formula:

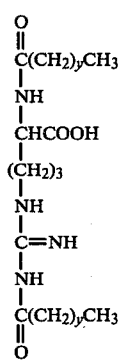

wherein y is an integer of from 0 to 28, or a pharmaceutically acceptable salt thereof.

23. A method for inhibiting acid production by microorganisms in the oral cavity which comprises introducing into the oral cavity a composition comprising from about 0.05 to about 10% of $N^\alpha,N^G$-diacyl derivative of arginine having the formula:

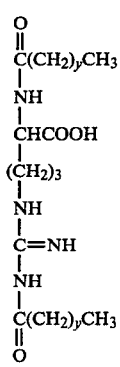

wherein y is an integer of from 4 to 18, or a pharmaceutically acceptable salt thereof, in combination with from about 0.001 to about 1.0% of a fluoride salt in a pharmaceutically acceptable polyol-containing vehicle.

* * * * *